(12) United States Patent
Polaschegg et al.

(10) Patent No.: US 7,276,042 B2
(45) Date of Patent: Oct. 2, 2007

(54) LOW HYDRAULIC RESISTANCE CARTRIDGE

(75) Inventors: Hans-Dietrich Polaschegg, Kostenberg (AT); Victor Gura, Beverly Hills, CA (US)

(73) Assignee: National Quality Care, Inc., Beverly Hills, CA (US)

( * ) Notice: Subject to any disclaimer, the term of this patent is extended or adjusted under 35 U.S.C. 154(b) by 273 days.

(21) Appl. No.: 10/350,858

(22) Filed: Jan. 23, 2003

(65) Prior Publication Data

US 2004/0147900 A1 Jul. 29, 2004

(51) Int. Cl.
*A61M 37/00* (2006.01)
*B01D 39/00* (2006.01)
*A61M 1/00* (2006.01)

(52) U.S. Cl. .................... 604/6.09; 604/4.01; 604/5.01; 604/5.04; 210/645; 210/500.21; 210/503; 422/44

(58) Field of Classification Search ............... 604/4.01, 604/5.01, 6.09, 6.08; 422/44, 48; 210/233, 210/264, 279, 284, 285, 323.1, 321.64, 252, 210/257.2, 500.1, 503, 253, 504, 644–646, 210/263, 266, 283, 286–289
See application file for complete search history.

(56) References Cited

U.S. PATENT DOCUMENTS

| 3,664,506 | A | * | 5/1972 | Meunier et al. ............ 210/282 |
| 4,472,303 | A | * | 9/1984 | Tanihara et al. ............ 530/359 |
| 4,540,492 | A | * | 9/1985 | Kessler .................... 210/651 |
| 4,685,900 | A | * | 8/1987 | Honard et al. ............. 604/6.09 |
| 4,828,543 | A | * | 5/1989 | Weiss et al. ............... 604/6.09 |
| 5,185,086 | A | * | 2/1993 | Kaali et al. ................. 210/748 |
| 6,133,431 | A | * | 10/2000 | Yasuda et al. .............. 530/413 |
| 6,497,675 | B1 | * | 12/2002 | Davankov ................... 604/6.09 |
| 6,605,214 | B1 | * | 8/2003 | Taylor ....................... 210/232 |
| 6,796,944 | B2 | | 9/2004 | O'Mahony et al. |
| 6,858,139 | B2 | * | 2/2005 | Taylor ....................... 210/232 |
| 6,866,783 | B2 | * | 3/2005 | Baurmeister et al. ....... 210/649 |

OTHER PUBLICATIONS

Martin Roberts, "Wearable Artificial Kidneys for Continuous Dialysis," ASAIO Journal, 1993, p. 19-23.
A. Murisasco, et al; "Continuous Arterio-venous Hemofiltration in a Wearable Device to Treat End-stage Renal Disease," Trans Am Soc Artif Intern Organs, vol. XXXII, 1986, pp. 567.
A. Murisasco, et al, "A Continuous Hemofiltration System Using Sorbents for Hemofiltrate Regeneration," Clinical Nephrology, vol. 26, Supp. No. 1—1986, pp. S53-S57.
Arnold J. Lande', et al, "In Search of a 24 Hours Per Day Artificial Kidney," Journal of Dialysis, 1(8), 1977, pp. 805-823.

* cited by examiner

*Primary Examiner*—Tatyana Zalukaeva
*Assistant Examiner*—Leslie R. Deak
(74) *Attorney, Agent, or Firm*—Howison & Arnott, L.L.P.

(57) ABSTRACT

A cartridge for treating medical or biological fluid includes a first cap having an inlet for the fluid, a container including a plurality of compartments and a second cap including an outlet for the fluid, wherein each compartment contains a plurality of particles, wherein the fluid is adapted to flow through the compartments and react with the plurality of particles.

20 Claims, 8 Drawing Sheets

LOW HYDRAULIC RESISTANCE CARTRIDGE

FIELD OF THE INVENTION

The present invention is directed to cartridges. More particularly, the invention concerns to a low hydraulic resistance cartridges for use in processing medical or biological fluids.

BACKGROUND OF THE INVENTION

Cartridges are commonly used in the medical and pharmaceutical field for the modification of the content of medical or biological fluids such as blood, blood plasma, blood serum, ultrafiltrate, dialysate, irrigation fluid and infusion fluid. Usually, a cartridge contains particles in various forms that react with fluid, which is pumped through an inlet in the cartridge. Cartridges can be used during dialysis to adsorb impurities from a patient's blood. Other cartridge uses include; (2) exchanging substances from fluid against others contained in the particles; (3) modifying substances in fluid by catalytic or enzymatic reactions; and (4) releasing substances into fluid.

During adsorption, molecules of medical or biological fluid flow through the cartridge between the particles and diffuse in all directions. Some molecules are diffused in the direction of a particle and are absorbed. Diffusion time is largely dependent upon particle size such that large diameter particles require a much longer diffusion time for complete adsorption. On the other hand, the use of small diameter particles causes an increase in a hydraulic pressure drop between the cartridge inlet and outlet. For practical purposes such as power requirements, this pressure drop must be limited, especially when a plurality of cartridges are used in series.

In view of the above, there is a need for a cartridge design that reduces diffusion time with the use of small particles, but does not create a substantial pressure drop between the cartridge inlet and cartridge outlet.

SUMMARY OF THE INVENTION

The present invention alleviates to a great extent the above-noted and other disadvantages by providing a low hydraulic resistance cartridge that permits the use of small sized particles, yet does not create a substantial pressure drop between the cartridge's inlet and outlet. This is achieved by choosing a cartridge geometry having a large header surface area and a short perfusion distance.

One aspect of the present invention involves a cartridge for treating medical or biological fluid including a first cap having an inlet for the fluid, a container including a plurality of compartments and a second cap including an outlet for the fluid, wherein each compartment contains a plurality of particles, wherein the fluid is adapted to flow through the compartments and react with the plurality of particles.

Another aspect of the present invention involves a cartridge for treating medical or biological fluid including a first cap having an inlet for the fluid, a container including a plurality of compartments and a second cap including an outlet for the fluid, wherein each compartment contains a plurality of particles, wherein the fluid is adapted to flow through the compartments and react with the plurality of particles, further comprising a first filter located between the first cap and the container, wherein the filters are adapted to prevent particles from exiting the cartridge.

A further aspect of the present invention involves a cartridge for treating medical or biological fluid including a first cap having an inlet for the fluid, a container including a plurality of compartments and a second cap including an outlet for the fluid, wherein each compartment contains a plurality of particles, wherein the fluid is adapted to flow through the compartments and react with the plurality of particles, wherein the fluid contains impurities and the fluid reacts with the particles such that at least some of the impurities are adsorbed by the particles, wherein the fluid is blood and the particles include activated carbon for removing impurities from the blood.

Yet another aspect of the present invention involves a cartridge for treating medical or biological fluid including a first cap having an inlet for the fluid, a container including a plurality of compartments and a second cap including an outlet for the fluid, wherein each compartment contains a plurality of particles, wherein the fluid is adapted to flow through the compartments and react with the plurality of particles, wherein physiological ions are loaded onto zirconium phosphate particles, wherein the fluid contains impurities, wherein the fluid reacts with the particles such that at least some of the impurities diffuse to the particles and replace at least some of the physiological ions and wherein at least some of the physiological ions diffuse into the fluid.

A further aspect of the present invention involves a cartridge for treating medical or biological fluid including a first cap having an inlet for the fluid, a container including a plurality of compartments and a second cap including an outlet for the fluid, wherein each compartment contains a plurality of particles, wherein the fluid is adapted to flow through the compartments and react with the plurality of particles, wherein a beneficial or benign substance such as urease is loaded onto the particles and the fluid reacts with the particles, wherein the fluid contains impurities and the beneficial or benign substance modifies the impurities by enzymatic reactions.

An additional aspect of the present invention involves an apparatus for treating medical or biological fluid, comprising a plurality of cartridges connected in parallel, each cartridge comprising a first cap including an inlet for the fluid, a container including a plurality of compartments and a second cap including an outlet for the fluid, wherein each compartment contains a plurality of particles, wherein a beneficial or benign substance such as an antibiotic is loaded onto the particles, wherein the fluid is adapted to flow through the compartments and react with the plurality of particles.

A further aspect of the present invention involves an apparatus for treating medical or biological fluid, comprising a plurality of cartridges connected in series, each cartridge comprising a first cap including an inlet for the fluid, a container including a plurality of compartments and a second cap including an outlet for the fluid, wherein each compartment contains a plurality of particles, wherein the fluid is adapted to flow through the compartments and react with the plurality of particles.

These and other features and advantages of the present invention will be appreciated from review of the following detailed description of the invention, along with the accompanying figures in which like reference numerals refer to like parts throughout.

DETAILED DESCRIPTION OF THE PREFERRED EMBODIMENTS

In the following paragraphs, the present invention will be described in detail by way of examples with reference to the attached drawings. Throughout this description, the preferred embodiment and examples shown should be considered as exemplars, rather than as limitations on the present invention. As used herein, the "present invention" refers to any one of the embodiments of the invention described herein, and any equivalents. Furthermore, reference to various feature(s) of the "present invention" throughout this document does not mean that all claimed embodiments or methods must include the referenced feature(s).

Figures 1, 2:
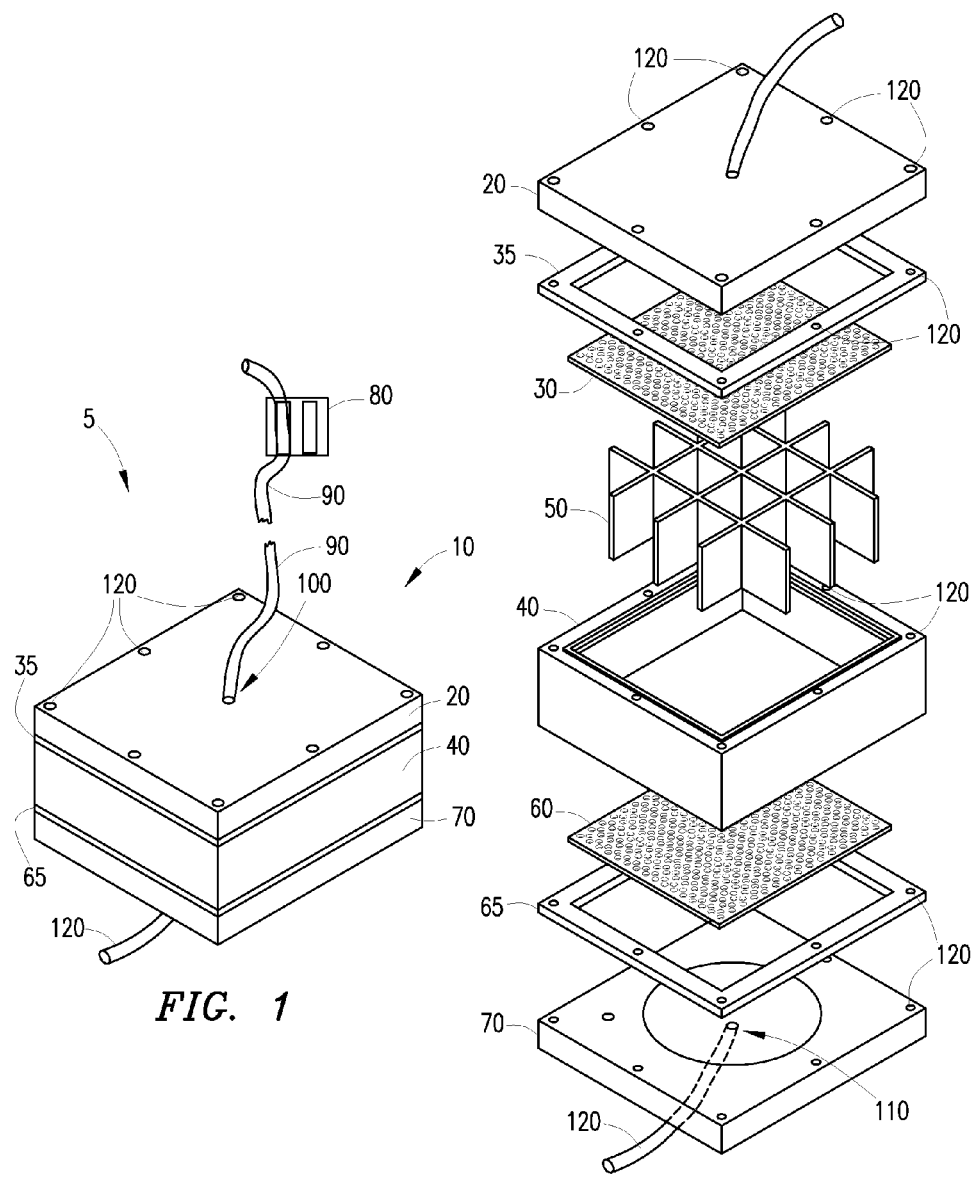
FIG. 1 is a perspective view of an embodiment of an assembly in accordance with the present invention.
FIG. 2 is a perspective view of an embodiment of an assembly in accordance with the present invention.

As seen in FIG. 1, the present invention is directed toward a cartridge 10 for the treatment of medical fluid or biological fluids. The cartridge 10, which may be rigid or flexible, includes at least one inlet 100 and one outlet 110. In some embodiments, the cartridge 10 is made of a strong durable plastic such as clear polished acrylic.

As seen in FIGS. 1-10, a system 5 for treating medical or biological fluid comprises a cartridge 10 having a plurality of components including a first cap 20, a first filter 30, a container 40, a plurality of separators 50, a second filter 60 and a second cap 70. During treatment, a pump 80 forces the fluid through an inlet tube 90 and into the cartridge 10 via inlet 100 in the first cap 20. After treatment, the fluid flows out of the cartridge 10 through outlet 110 in the second cap 70 and into an outlet tube 120. To prevent fluid leakage, first and second gaskets 35,65 surround the first and second filters 30,60, respectively. According to one embodiment, the gaskets 35,65 are made of silicone rubber.

Figure 3:
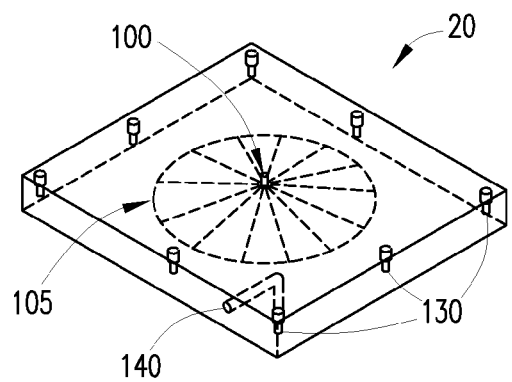
FIG. 3 is a perspective view of an embodiment of an assembly in accordance with the present invention.
Figure 5:
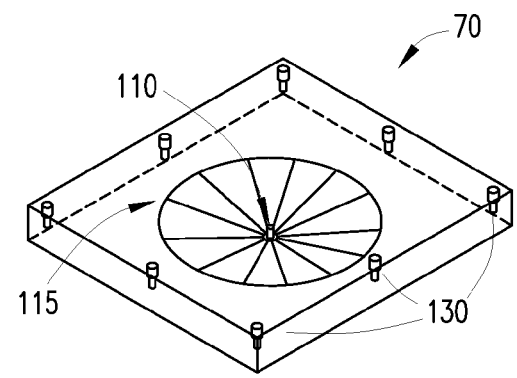
FIG. 5 is a perspective view of an embodiment of an assembly in accordance with the present invention.

The caps 20,70, gaskets 35,65 and container 40 include a plurality of apertures 120 dimensioned to receive fasteners 130. As seen in FIGS. 3 and 5, a tool 140 may be used to tighten the fasteners 130. Both the fasteners 130 and apertures 140 may be threaded to facilitate attachment.

Figure 4:
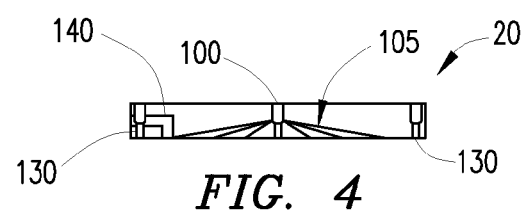
FIG. 4 is a cross-sectional view of an embodiment of an assembly in accordance with the present invention.
Figure 6:
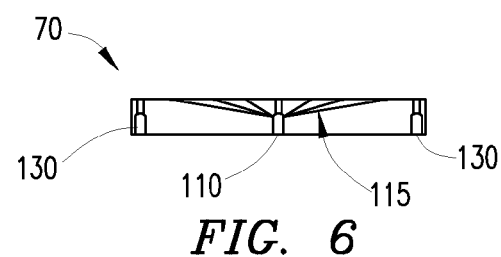
FIG. 6 is a cross-sectional view of an embodiment of an assembly in accordance with the present invention.
Figure 7:
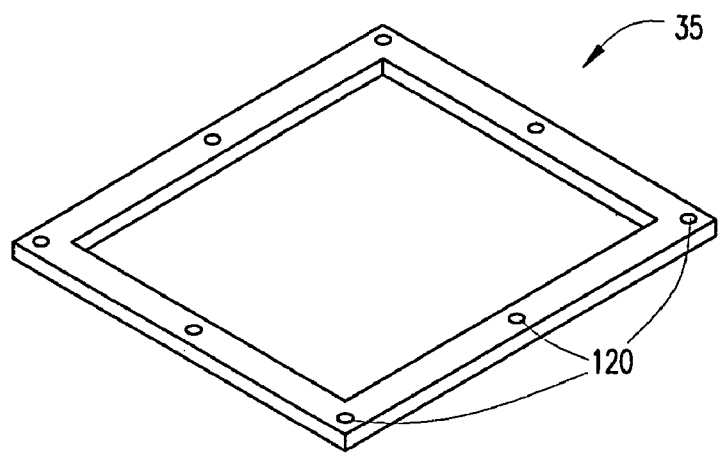
FIG. 7 is a perspective view of an embodiment of an assembly in accordance with the present invention.
Figure 8:
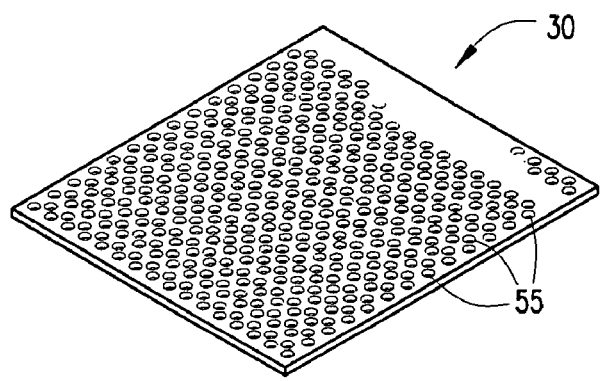
FIG. 8 is a perspective view of an embodiment of an assembly in accordance with the present invention.
Figure 9:
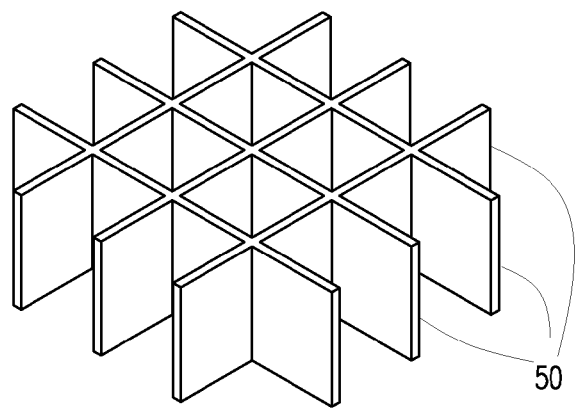
FIG. 9 is a perspective view of an embodiment of an assembly in accordance with the present invention.
Figure 10:
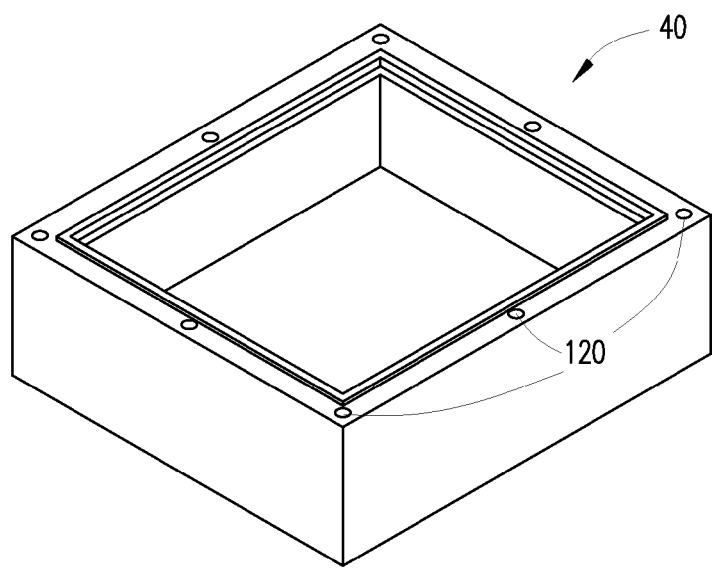
FIG. 10 is a perspective view of an embodiment of an assembly in accordance with the present invention.

As seen in FIGS. 2-4, the first cap 20 includes fluid inlet 100 and a conical section 105. After the fluid is pumped through the inlet 100, the conical section 105 helps distribute the fluid substantially evenly onto the first filter 30. Conversely, as seen in FIGS. 5 and 6, the second cap 70 includes a conical section 115 for funneling the fluid into the outlet 110 after treatment.

As seen in FIGS. 1, 2, 7 and 8, the gaskets 35,65 are dimensioned to fit around the perimeter of the filters 30,60 to prevent leakage between the container 40 and the caps 20,70. The filters 30,60 include a plurality of apertures 55 shaped and sized to permit the passage of fluid while filtering out larger impurities in the fluid. The first filter 30 also helps evenly distribute the fluid before it enters the container 40, which can reduce channeling and pressure drops within the cartridge 10. The second filter 60 prevents particles from the container 40 from exiting the cartridge 10 through the second cap 70.

Figure 11:
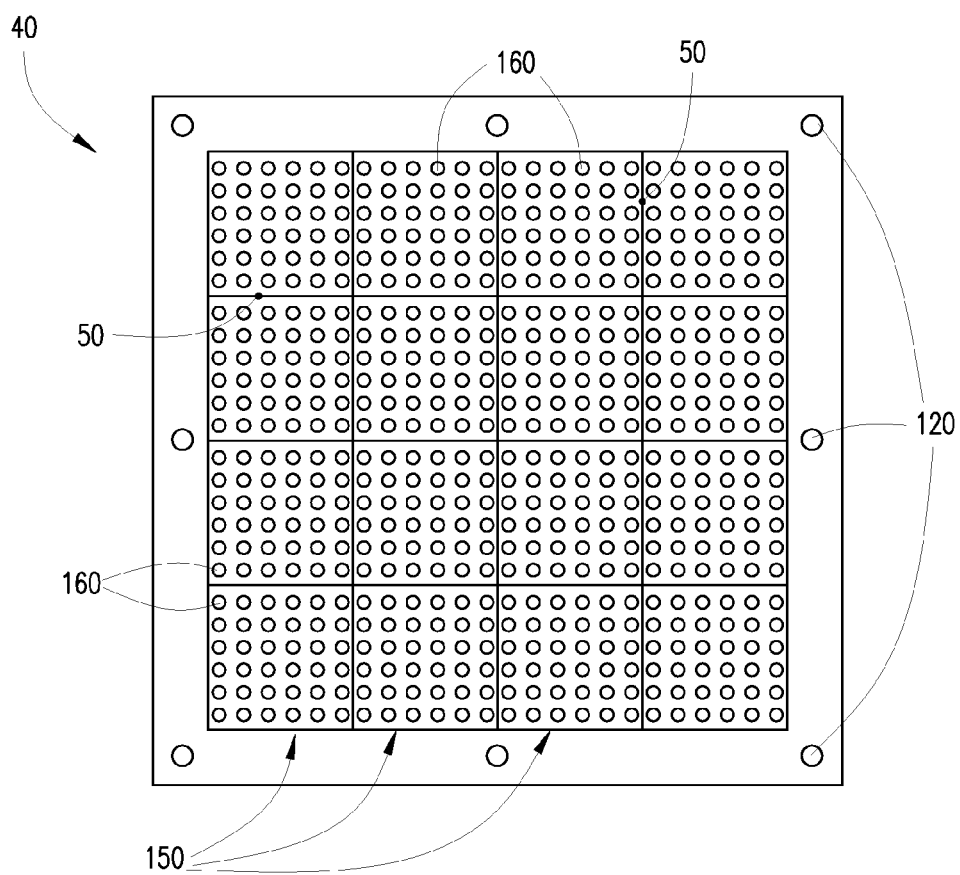
FIG. 11 is a top view of an embodiment of an assembly in accordance with the present invention.
Figure 12:
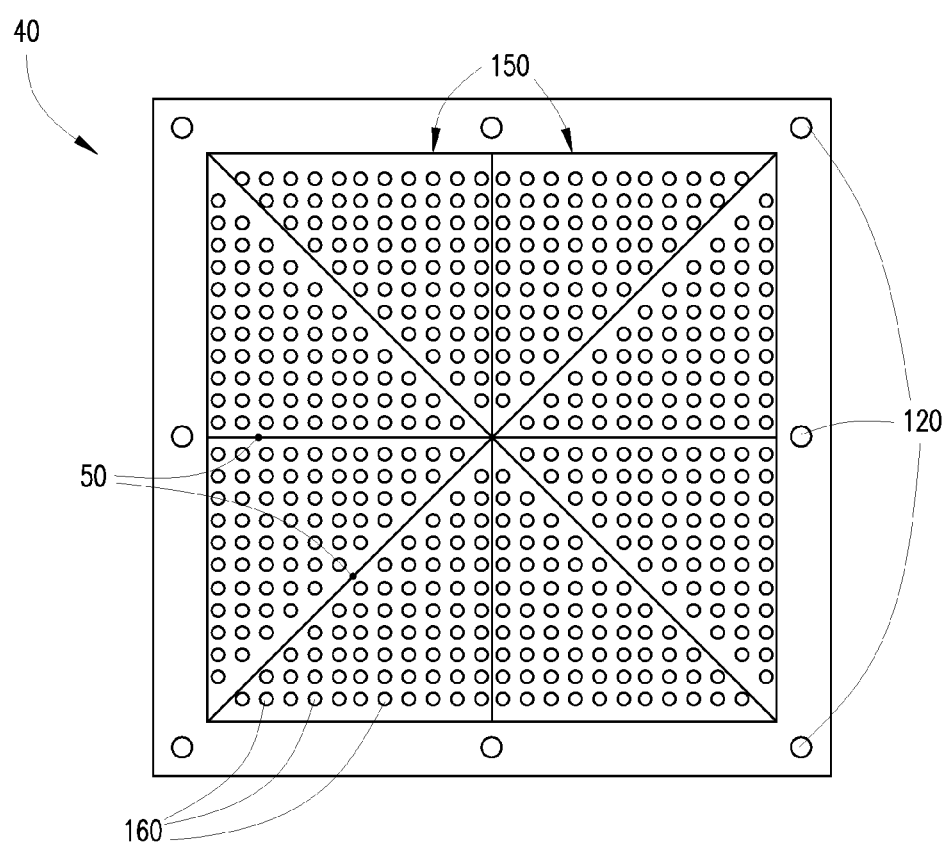
FIG. 12 is a top view of an embodiment of an assembly in accordance with the present invention.

As seen in FIGS. 9-12, the separators 50 divide the container 40 into a plurality of compartments 150. As seen in FIG. 11, according to one embodiment, the separators 50 are arranged as a grid forming box-shaped compartments 150. However, as would be understood by one of ordinary skill in the art, compartments of differing shapes and sizes could be utilized without departing from the scope of the present invention. As an example, the embodiment depicted in FIG. 12 features a plurality of separators 50 arranged at different angles such that the container 40 is divided into compartments 150 having a triangular cross-section.

The separators 50 allow the passage of fluid, but not solids. Each compartment 150 is filled with particles 160 of solid matter adapted to treat the medical or biological fluid. The particles 160 may be in the form of small substances including, but not limited to, granules of any shape, spherical beads, fibers, capillaries, porous blocks and gels.

The rate of diffusion is dependent upon the molecular weight of the substance to be adsorbed, the temperature and the diffusion distance. The use of porous particles 160 will significantly increases the effective surface area for adsorption or reaction. However, this will reduce the rate of diffusion since, in order to achieve adsorption, a substance from the fluid must diffuse to the surface of a particle 160, enter a pore, then diffuse to the inner structure of the particle 160. When medical or biological fluid is pumped through the cartridge 10, the molecules of the substance to be adsorbed are moving with the fluid within channels between the particles 160. These molecules diffuse randomly in all directions. Some molecules diffuse in the direction of a particle 160, enter a pore and are adsorbed.

Since larger particles 160 have longer diffusion distances, they also require much greater diffusion times. If the particle size is increased, the diffusion time will increase exponentially. On the other hand, if the particle size is reduced, the diffusion time will decrease significantly. Hence, the use of smaller particles is preferred for increasing the rate of diffusion and the surface are for adsorption. However, the use of smaller particles greatly increases the hydraulic pressure drop between the cartridge inlet 100 and cartridge outlet 110.

The pressure drop at the cartridge outlet 110 results from the resistance of the particles 160 within the container 40 as the fluid flows through the container 40. Preferably, pressure drops should be limited since larger pressure drops require more powerful pumps and stronger tubing, especially when a plurality of cartridges 10 are used in series.

Figure 13:
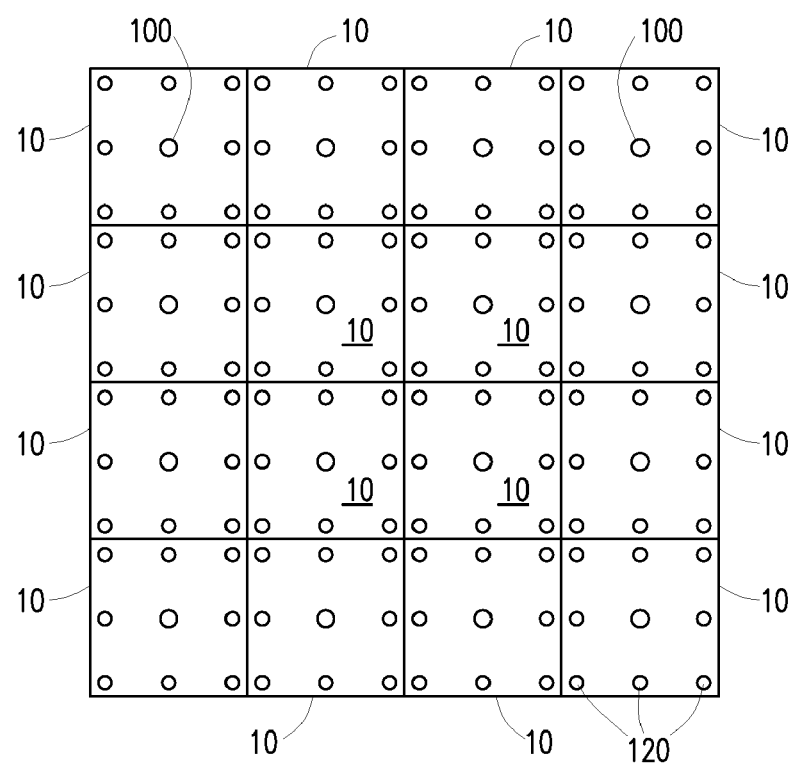
FIG. 13 is a top view of an embodiment of an assembly in accordance with the present invention.

The low hydraulic resistance cartridge 10 of the present invention permits the use of smaller sized particles 160, yet does not create a substantial pressure drop between the cartridge inlet 100 and cartridge outlet 110. This is achieved by choosing a cartridge geometry having a maximum header surface area and a minimum perfusion distance. For example, as seen in FIG. 13, the maximum header surface is accomplished by passing the fluid through the 16 compartments 150 of particles in parallel. The short perfusion distance is accomplished by choosing a cartridge geometry featuring a minimal distance between the cartridge inlet 100 and the cartridge outlet 110. Such a cartridge design may facilitate channeling, which is the formation of fluid conduits through the particles 160.

Channeling can dramatically decrease the effectiveness of the cartridge 10. It may occur when the packing of the particle material is not sufficiently dense. Since the particle material may shrink or swell during use, the cartridge geometry must also be capable of volume changes without causing channeling. According to the present invention, the instance of channeling is greatly reduced by separating the container 40 into a plurality of compartments 150. Because the particles 160 are within the confined space of the small compartments 150, channeling paths are far less likely to develop than if the particles 160 were otherwise loose within the container 40.

According to some embodiments, the cartridge 10 is used for adsorption, wherein the container 40 is a fixed bed adsorber wherein the particles 160 are fixed within the compartments 150. To prevent channeling, the compartments 150 should be substantially uniformly filled with particles 160, if possible.

In adsorption, substances from the medical or biological fluid diffuse to the surface of the particles 160 where they are adsorbed. To increase the active surface area for adsorption, the particles 160 are porous. Activated carbon is frequently used as an adsorption material to remove poisons from the fluid.

According to other embodiments, the cartridge 10 is used for substance exchange. In substance exchange, substances from the medical or biological fluid diffuse to the particles 160 and replace substances attached to the particles 160. The latter substances diffuse away from the particles 160 and into the fluid. Zirconium phosphate can be used as a substance exchange carrier for exchanging ammonium ions against sodium ions.

According to other embodiments, the cartridge 10 is used for substance release. In substance release, beneficial or benign substances attached to the particles 160 are released when they come in contact with the fluid. As an example, urease, insulin or antibiotics can be used as substance release materials for modifying impurities within the fluid by enzymatic reactions.

Figure 14:
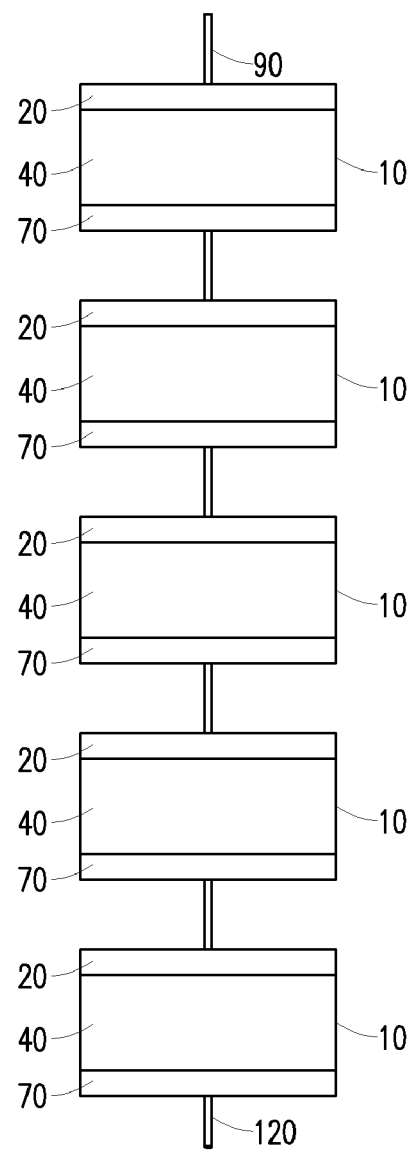
FIG. 14 is a front view of an embodiment of an assembly in accordance with the present invention.

As seen in FIG. 13, according to one embodiment, a plurality of cartridges 10 are connected in parallel, whereby medical or biological fluid from a single source flows at a substantially equal rate through each of the cartridge inlets 100. By testing this embodiment using an injected substance, it has been shown that using a plurality of cartridges 10 in parallel causes a lower pressure drop and significantly less channeling. During such testing, the injected substance is injected at the cartridge inlet 100 and a sensor is located at the cartridge outlet 110 so that the pressure drop can be measured. As seen in FIG. 14, according to another embodiment, a plurality of cartridges 10 are connected in series, wherein fluid is pumped into the plurality of cartridges 10 through inlet tube 90. The fluid exits via outlet tube 120 after flowing through each cartridge 10 in the series of cartridges 10.

According to some embodiments, the cartridge contains five layers including an activated charcoal layer, a urease layer, a zirconium phosphate layer, a hydrous zirconium oxide layer and an activated carbon layer. Those of ordinary skill in the art will recognize that this cartridge is similar to the commercially available Recirculating Dialysis (REDY) System. However, as would be understood by one of ordinary skill in the art, any number of additional or alternative cartridge layers could be employed without departing from the scope of the present invention.

In some embodiments, to reduce channeling, the carbon particles are mixed with the urease particles. In other embodiments, the carbon particles are mixed with the rest of the particles and/or mixed with other fine powders.

The fluid pump 80 forces medical or biological fluid such as blood through the cartridge 10. This pump 80 may be chosen from a group including, but not limited to, a shuttle pump, piston pump, roller pump and a centrifuge pump. Conventional power sources such as batteries can be used to power the pump 80. Optionally, small fuel cells can be used to provide a higher power density. According to one embodiment, a shuttle pump is used to pump the fluid because it saves energy and because it automatically stops pumping if the fluid contains too much gas. This provides an inherent safety feature since the shuttle pump cannot function properly if a certain amount of gas is present.

During use of the cartridge 10, gas bubbles in the form of carbon dioxide, which is a bi-product of the conversion of urea to ammonium by urease, may be produced. Since these gas bubbles block the flow of fluid, the efficiency of the system 5 is compromised. According to some embodiments, the carbon dioxide is removed as soon as it is produced using a hydrophobic membrane that allows the passage of gas, but not fluid. The removed carbon dioxide can then be used to reduce the pH of the urea containing fluid before it reacts with urease in order to stabilize the pH at value of about 7 or 8. According to other embodiments, the carbon dioxide is removed using an air pump or, if positive pressure is maintained in the cartridge relative to the environment, is released passively through the hydrophobic membrane using this pressure gradient.

In some embodiments, the medical or biological fluid is blood. To prevent the coagulation of the blood, an anticoagulent is constantly infused through the inlet tube 90. Suitable anticoagulants include, but are not limited to, heparin, prostacyclin, low molecular weight heparin, hirudin and sodium citrate.

Thus, it is seen that a low hydraulic resistance cartridge is provided. One skilled in the art will appreciate that the present invention can be practiced by other than the preferred embodiments which are presented in this description for purposes of illustration and not of limitation, and the present invention is limited only by the claims that follow. It is noted that equivalents for the particular embodiments discussed in this description may practice the invention as well.

What is claimed is:

1. A cartridge for treating medical or biological fluid comprising:
  a container housing defining a inner chamber having a chamber wall and an input end and an outlet end, the container housing having an inner chamber length from the input end to the outlet end such that the inner chamber width is at least three times larger than the inner chamber length, the inner chamber length measured in the general direction of fluid flow through the filtering apparatus between the input end and the outlet end;
  the input end having an outer wall and an inner wall, the inner wall defining an inwardly opening conical fluid distribution chamber having a fluid inlet at the apex of the conical fluid distribution chamber;

the outlet end having an outer wall and an inner wall, the inner wall defining an inwardly opening conical fluid collection chamber having a fluid outlet at the apex of the conical fluid collection chamber;

a plurality of fluid permeable separators extending inwardly beginning proximate to the inner wall and into the inner chamber, the separators defining a plurality of open ended compartments inside the container housing wherein fluid can flow through the separators and between the compartments and wherein solid particles are retained by the separators in the compartments, the compartments each having a compartment length in the general direction of fluid flow though the filter from the conical fluid distribution chamber to the conical fluid collection chamber, each compartment having a first open inlet end proximate to the conical fluid distribution chamber and a second open outlet end proximate the conical fluid collection chamber, each open inlet and outlet end of the compartments having a dimension across the open end that is equal to or shorter than the compartment length;

a first screen disposed between the conical fluid distribution chamber and the open inlet ends of the compartments, the screen distributing fluid flowing through the inlet and conical fluid distribution chamber to the open inlet ends of the compartments; and a second screen disposed between the conical fluid collection chamber and the open outlet ends of the compartments, the second screen retaining particles in the compartments and preventing particles in the compartments from entering the conical collection chamber.

2. The cartridge of claim 1, wherein the plurality of compartments are aligned in parallel.

3. The cartridge of claim 1 further comprising a plurality of adsorbent particles wherein the compartments are substantially filled with the adsorbent particles and wherein the particles adsorb impurities from a medical or biological fluid flowing therethough.

4. The cartridge of claim 3, wherein the particles are porous.

5. The cartridge of claim 1 further comprising a plurality of particles wherein the compartments are substantially filled with the particles and wherein the particles comprise one or more of activated charcoal, urease, zirconium phosphate, hydrous zirconium oxide and activated carbon.

6. The cartridge of claim 1 further comprising a plurality of particles wherein the compartments are substantially filled with the particles and wherein the particles comprise each of activated charcoal, urease, zirconium phosphate, hydrous zirconium oxide and activated carbon.

7. The cartridge of claim 1 wherein the input end further comprises a first removable cap.

8. cartridge of claim 1 wherein the outlet end comprises a second removable cap.

9. The cartridge of claim 1 further comprising a fluid pump connected to the input end.

10. The cartridge of claim 9 wherein the fluid pump is a shuttle pump.

11. A filtering apparatus for medical or biological fluid comprising:

a container housing defining a inner chamber having a chamber wall and an input end and an outlet end, the container housing having an inner chamber length from the input end to the outlet end such that the inner chamber width is at least three times larger than the inner chamber length, the inner chamber length measured in the general direction of fluid flow through the filtering apparatus between the input end and the outlet end;

a first cap removably and sealingly attached to the input end of the container housing, the first cap having a substantially flat outer wall and an inner wall, the inner wall defining an inwardly opening conical fluid distribution chamber having a fluid inlet at the apex of the conical fluid distribution chamber;

a second cap removably and sealingly attached to the outlet end of the container housing, the second cap having a substantially flat outer wall and an inner wall, the inner wall defining an inwardly opening conical fluid collection chamber having a fluid outlet at the apex of the conical fluid collection chamber;

a plurality of fluid permeable separators extending inwardly from the inner chamber wall and into the inner chamber and defining a plurality of open ended compartments inside the container housing wherein solid particles are retained by the separators in the compartments, the compartments each having a compartment length from the input end of the container housing to the outlet end of the container housing, each compartment having a first open inlet end proximate to the conical fluid distribution chamber and a second open outlet end proximate the conical fluid collection chamber, each open inlet and outlet end of the compartments having a dimension across the open end that is equal to or shorter than the compartment length;

a first screen disposed between the conical fluid distribution chamber and the open inlet ends of the compartments, the screen distributing fluid flowing through the inlet and conical fluid distribution chamber to the open inlet ends of the compartments; and a second screen disposed between the conical fluid collection chamber and the open outlet ends of the compartments, the second screen retaining particles in the compartments and preventing particles in the compartments from entering the conical fluid collection chamber.

12. The apparatus of claim 11 wherein the first screen is disposed between the conical fluid distribution chamber and the compartments and wherein the first screen is removable upon removing the first cap from the container housing.

13. The apparatus of claim 11 wherein the first screen is disposed between the conical fluid collection chamber and the compartments and wherein the second screen is removable upon removing the second cap from the container housing.

14. The apparatus of claim 11 wherein the fluid inlet and fluid outlet are disposed on a central axis of the container and wherein the compartments are symmetrically arranged around the axis.

15. The apparatus of claim 11 further comprising a solid particulate adsorption medium and wherein the compartments are substantially filled with the solid particulate adsorption medium.

16. The apparatus of claim 15 wherein the filter medium is selected from one or more of activated charcoal and activated carbon.

17. The apparatus of claim 16 wherein the release material comprises urease.

18. The apparatus of claim 15 further comprising a release material that modifies impurities in a medical or biological fluid flowing through the apparatus.

19. A filtering apparatus for medical or biological fluid comprising:

a container housing defining a inner chamber having a chamber wall and an input end and an outlet end, the container housing having an inner chamber length from the input end to the outlet end such that the inner chamber width is at least three times larger than the inner chamber length, the inner chamber length measured in the general direction of fluid flow through the filtering apparatus between the input end and the outlet end;

a first cap removeably and sealingly attached to the input end of the container housing, the first cap having a substantially flat outer wall and an inner wall, the inner wall defining an inwardly opening conical fluid distribution chamber having a fluid inlet at the apex of the conical distribution chamber;

a second cap removeably and sealingly attached to the outlet end of the container housing, the second cap having a substantially flat outer wall and an inner wall, the inner wall defining an inwardly opening conical fluid collection chamber having a fluid outlet at the apex of the conical collection chamber;

a plurality of fluid permeable separators extending inwardly from the inner chamber wall and into the inner chamber and defining a plurality of open ended compartments inside the container housing wherein fluid can flow through the separators and between the compartments and wherein solid particles are retained by the separators in the compartments, the compartments each having a compartment length from the input end of the container housing to the outlet end of the container housing, each compartment having a first open inlet end proximate to the conical fluid distribution chamber and a second open outlet end proximate the conical collection chamber, each open inlet and outlet end of the compartments having a dimension across the open end that is equal to or shorter than the compartment length;

a first screen disposed between the conical fluid distribution chamber and the open inlet ends of the compartments, the screen distributing fluid flowing through the inlet and conical fluid distribution chamber to the open inlet ends of the compartments;

a second screen disposed between the conical fluid collection chamber and the open outlet ends of the compartments, the second screen retaining particles in the compartments and preventing particles in the compartments from entering the conical collection chamber;

a first plurality of fasteners securing the first cap to the input end of the container housing with the first screen disposed between the conical fluid distribution chamber and the compartments and wherein the first screen is removable upon removing the fasteners and removing the first cap from the container housing; and a second plurality of fasteners securing the second cap to the outlet end of the container housing with the second screen disposed between the conical fluid collection chamber and the compartments and wherein the second screen is removable upon removing the fasteners and removing the second cap from the container housing.

20. The cartridge of claim 19 wherein the fasteners are arranged around the perimeter of the first and second caps.

* * * * *